United States Patent
Villotti, Jr.

[11] Patent Number: 5,643,232
[45] Date of Patent: Jul. 1, 1997

[54] PAP SMEAR GLOVE

[76] Inventor: James P. Villotti, Jr., 1832 Whispering Pines Cir., Englewood, Fla. 34223

[21] Appl. No.: 588,817

[22] Filed: Jan. 19, 1996

[51] Int. Cl.⁶ ............................. A41D 19/00; A61B 10/00; A61M 35/00
[52] U.S. Cl. ..................... 604/292; 604/290; 128/756; 2/161.7
[58] Field of Search ..................... 604/289, 292, 604/310, 290; 2/161.7, 163, 168, 21; 128/756, 775, 778; 606/119

[56] References Cited

U.S. PATENT DOCUMENTS

| | | |
|---|---|---|
| 411,572 | 9/1889 | Bobo . |
| 622,386 | 4/1899 | Peery . |
| 683,869 | 10/1901 | Weichert . |
| 809,119 | 1/1906 | Leuchs . |
| 1,010,283 | 11/1911 | Loy . |
| 1,200,596 | 10/1916 | Daly .............................. 2/21 |
| 1,220,007 | 3/1917 | Rowley .......................... 2/21 |
| 1,261,706 | 4/1918 | Condley et al. ................ 2/21 |
| 1,726,728 | 9/1929 | Adams . |
| 1,979,130 | 8/1934 | Wiley . |
| 2,847,012 | 8/1958 | Eastman ....................... 604/289 |
| 3,027,794 | 4/1962 | Chute . |
| 3,126,890 | 3/1964 | Deming, Sr. ................. 2/161.7 |
| 4,127,222 | 11/1978 | Adams ............................. 2/21 |
| 4,754,764 | 7/1988 | Bayne ........................... 606/119 |
| 4,759,376 | 7/1988 | Stormby ....................... 606/119 |
| 5,045,073 | 9/1991 | Wagner ........................ 604/310 |
| 5,191,899 | 3/1993 | Strickland et al. ........... 128/756 |
| 5,234,142 | 8/1993 | Loewen et al. ................. 2/21 |
| 5,345,612 | 9/1994 | Stein . |
| 5,428,841 | 7/1995 | Stein . |
| 5,496,337 | 3/1996 | Brown .......................... 2/163 |

Primary Examiner—John G. Weiss
Assistant Examiner—David J. Cho
Attorney, Agent, or Firm—Hoffman, Wasson & Gitler

[57] ABSTRACT

A glove for performing pap smear cell sampling is provided having a tapered surgical glove, with a tapered, feathered, or brush-like tip projecting from the index finger. The projection can have a variety of configurations, such as a cyto brush applique attached to the end of the glove. The device is used by a health care professional during a pelvic examination. The tip can be manipulated into and onto the endocervix and cervix and withdrawn after a half-turn circular motion and smeared in the traditional technique onto existing slides for pathological examination.

16 Claims, 4 Drawing Sheets

PAP SMEAR GLOVE

BACKGROUND OF THE INVENTION

1. Field of the Invention

The present invention pertains to a glove for use in performing pap smears. In particular, the present invention relates to a glove having an extension projecting from the index finger.

2. Description of the Prior Art

Pap smear procedures are commonly performed on women as part of routine examinations. A speculum is the instrument of choice for such examinations. However, for women who have stenotic and atrophic vaginas, a speculum cannot be easily passed to perform a pap smear.

The growing elderly female population, while needing pap smears as part of their regular check ups, present a difficult problem since a speculum cannot be easily passed to reach the cervix and endocervix. As a result, costly referrals or anesthesia, as well as, concurrent embarrassment and undue discomfort are incurred. As a consequence, many women who are difficult to sample do not get sampled as often as they should and avoid repeat follow-up tests.

In addition to elderly women, young women who have not experienced sexual relations or penetration, present similar difficult problems in achieving adequate pap smear sampling.

A variety of devices have been developed for various medical procedures. For example, U.S. Pat. No. 411,572 to Bobo discloses an instrument that can be used and applied to a health care professional's hands and serve as an obstetrical forceps.

Another device is disclosed in U.S. Pat. No. 2,847,012; which teaches a device for rupturing amniotic membranes. The device includes a glove-like cover for a portion of the hand having a hardened extension affixed to the end thereof, which can be manipulated to engage with and rupture the membrane at the cervix in an obstetrical operation.

U.S. Pat. No. 809,119 to Leuchs, and U.S. Pat. No. 622,386 to Peery both pertain to curettes which can be applied to the forefinger to remove placental residues from the uterine cavity. Both curettes fit over the index finger and provide a finger-nail-like extension.

SUMMARY OF THE INVENTION

In view of the foregoing, it is an object of the present invention to overcome the drawbacks of connection speculum.

Another object of the present invention is to provide a device which increases the ease with which a pap smear procedure can be performed.

Yet another object of the present invention is to provide a device which is effective for performing pap smear procedures on elderly women and young women yet to experience intercourse.

Another object of the present invention is to provide a device for performing pap smears which is inexpensive and is easy to use.

The present invention is a glove, preferably a rubber surgical glove, with a tapered, feathered, or brush-like tip projecting from the index finger. The projection can have a variety of configurations, such as a cyto brush applique attached to the end of the glove. The device is used by a health care professional during a pelvic examination. The tip can be manipulated into and onto the endocervix and cervix and withdrawn after a half-turn circular motion and smeared in the traditional technique onto existing slides for pathological examination.

BRIEF DESCRIPTION OF THE DRAWINGS

These and other attributes of the present invention will be described with respect to the drawings in which.

DETAILED DESCRIPTION OF THE PREFERRED EMBODIMENTS

Figure 1:
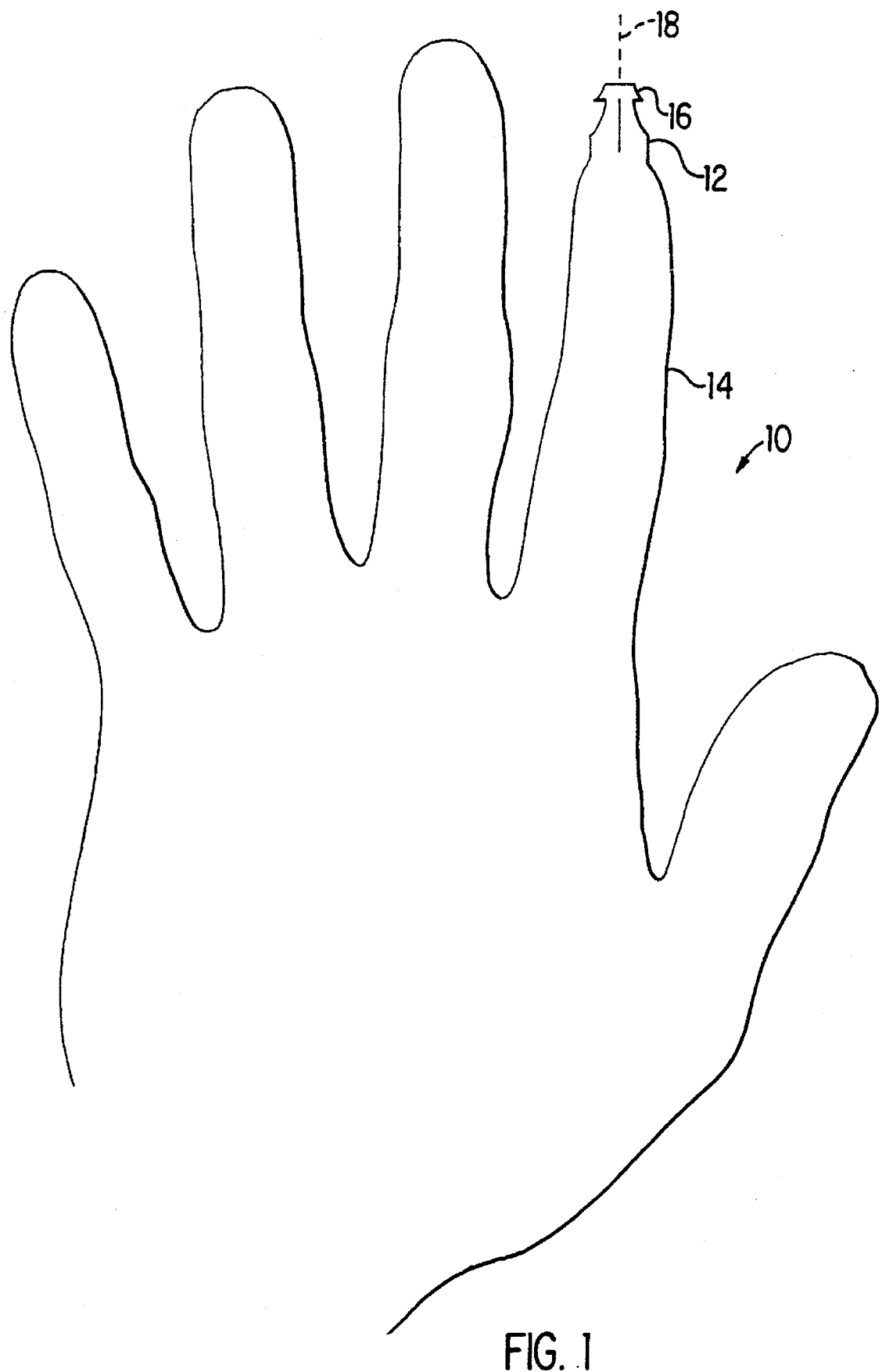
FIG. 1 is a side view of a first embodiment of the present invention.
Figure 2:
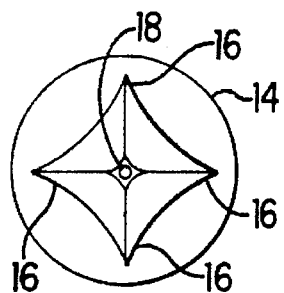
FIG. 2 is a top view of the glove shown in FIG. 1.

Referring to FIG. 1, the present invention includes a rubber surgical glove 10, which is commonly used to ensure sterility and prevent the spread of disease in almost all procedures. A projection 12 extends from a finger 14 of the glove 10, preferably the index finger. The projection 12 is tapered, getting narrower from the base on the index finger 14. As shown in FIG. 2, the projection 12 has four extensions 16, projecting radially outward from the axis of the projection 12. The index finger 14 and projection 12 share a common axis 18 to aid and facilitate the pap smear test operation.

In operation, the health-care professional wearing the glove 10, inserts the index finger 14 into the patients vagina. The projection reaches into the vaginal cavity, and is manipulated into and onto the endocervix and cervix. Once in place, the index finger is rotated a half turn in a circular motion about the axis 18, so that the extension 18 remove a sample from the patient. The health-care professional then removes the hand and the sample is smeared in the traditional technique onto a slide for pathological examination.

The projection 12 may be made from hardened plastic or other material, and may be affixed with glue to the index finger 14, or other such adhesive, or the projection 12 may be formed integrally with the glove 10.

Figure 3:
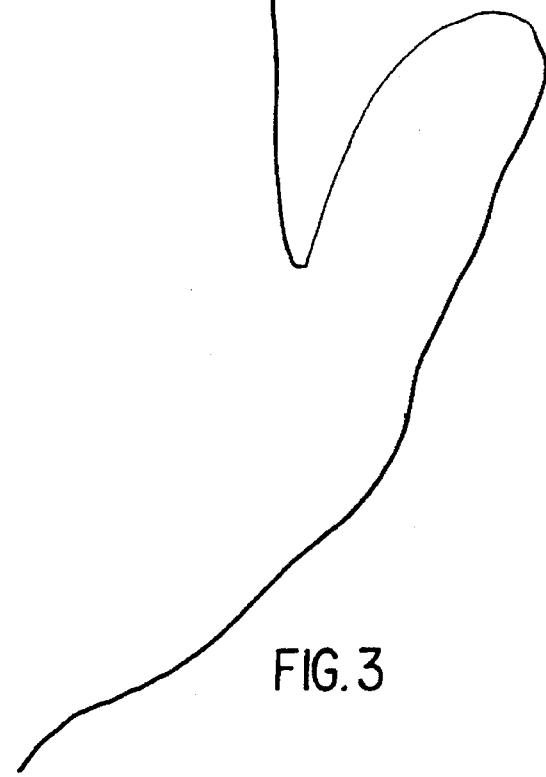
FIG. 3 is a second embodiment of the present invention having a cyto brush-like projection.

FIG. 3 shows a second embodiment where the projection 12 is replaced with a cyto brush applique 20 the removal of material is performed in similar technique at the first embodiment.

Figure 4:
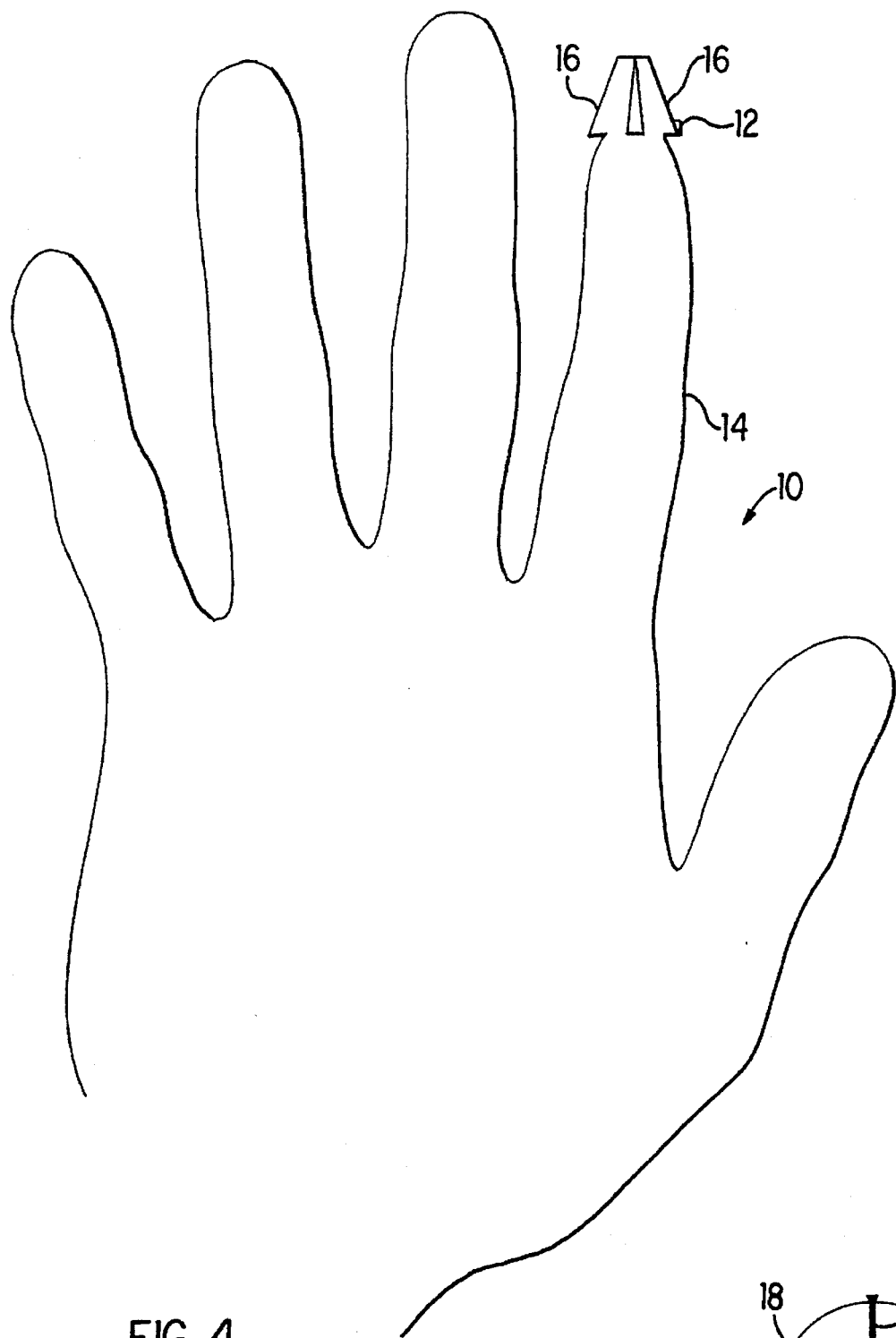
FIG. 4 is a side view of a third embodiment of the present invention.

FIG. 4 shows a third embodiment of the present invention similar to the first embodiment. The projection 12, in FIG. 4, does not taper like the first embodiment. Instead, the extensions 16, extending radially outward, extend from the tip of the index finger 14. The projection 12 is made from thickened hardened rubber or plastic.

Figure 5:
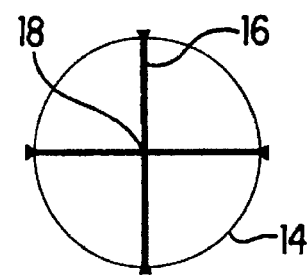
FIG. 5 is a top view of the embodiment shown in FIG. 4.

FIG. 5 shows a top view of the third embodiment from which it can be seen that the projections meet at the axis 18. This embodiment can also be used to scrape skin, mucous membranes of the mouth or other similar parts of a patient.

Figure 6:
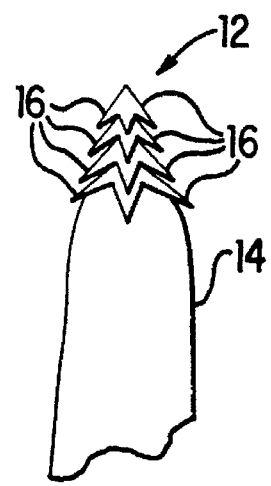
FIG. 6 is side view of a fourth embodiment of the present invention.

FIG. 6 shows a side view of a fourth embodiment of the present invention, in which the projection 12 includes multiple rows of extensions 16. The illustrated embodiment has four rows of extensions 17, and is used in the same manner as the first embodiment.

Figure 7:
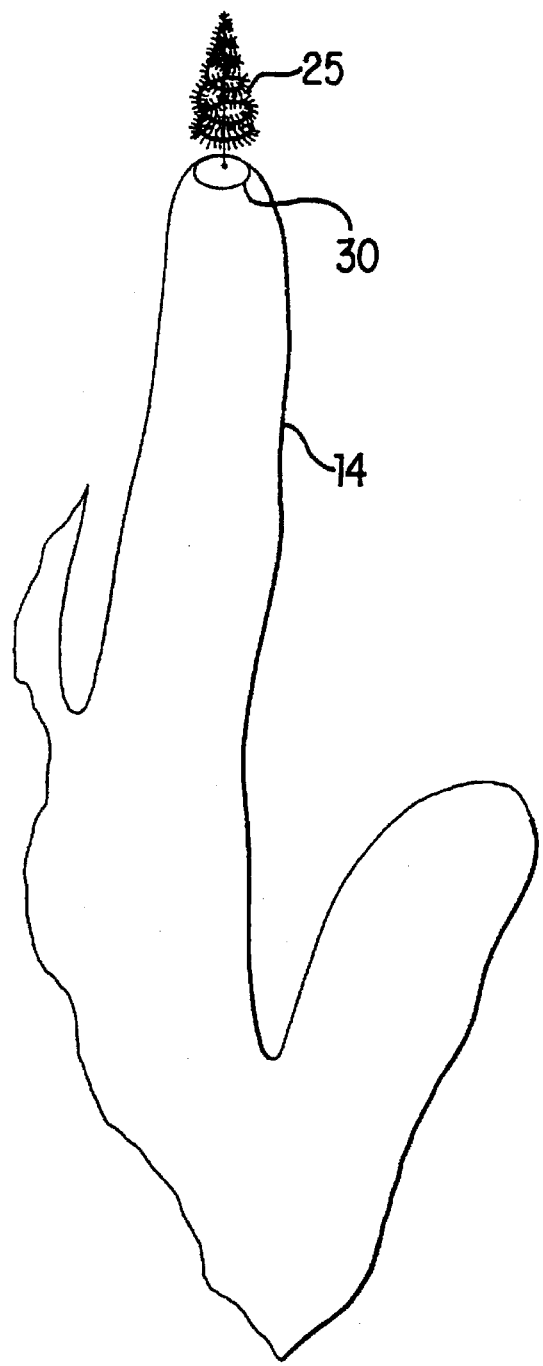
FIG. 7 is a side view of a fifth embodiment of the present invention.

FIG. 7 shows a fifth embodiment where the projection 12 is replaced with a spiral brush 25 extending along the axis of the index finger 14. The spiral brush 25 can be attached in the same manner as the projection 12, or by peel-off sticker tape 30. Once again, the brush 25 is used in the same manner as the first embodiment.

Having described an embodiment of the present invention, it is believed that other modifications, variations and changes will be suggested to those skilled in the art in view of the description set forth above. It is therefore to be understood that all such variations, modifications are believed to fall within the scope of the invention as defined in the appended claims.

What is claimed is:

1. A device for performing pap smear sampling comprising:
    a glove having at least one finger; and
    a substantially rigid projection extending from tip of said finger substantially parallel to an axis of said finger, said projection having multiple extension, extending radially from said axis for removing a sample from a patient.

2. The device as claimed in claim 1, wherein said glove is a rubber glove.

3. The device as claimed in claim 1, wherein said projection and said finger share a common axis.

4. The device as claimed in claim 1, wherein said device comprises at least three extensions.

5. The device as claimed in claim 1, wherein said device comprises four extensions.

6. The device as recited in claim 1, wherein said projection tapers away from said finger.

7. The device as recited in claim 1, wherein said extensions are disposed on an end of said projection opposite another end of said projection attached to said finger.

8. The device as recited in claim 1, wherein said projection and said glove are integrally formed.

9. The device as recited in claim 1, wherein said projection is a cyto brush applique.

10. The device as recited in claim 1, wherein said projection is a spiral brush.

11. The device as recited in claim 1, wherein said projection is made from rubber.

12. The device as recited in claim 1, wherein said projection is made from plastic.

13. The device as recited in claim 1, wherein said projection has an axis coextensive with an axis of said finger.

14. The device as recited in claim 1, wherein said projection has multiple rows of said extensions.

15. The device as recited in claim 1, wherein said finger is an index finger.

16. A method of performing a pap smear sampling procedure using a device for performing pap smear sampling comprising a glove; and a projection extending from a finger of said glove substantially parallel to an axis of said finger, said projection having multiple extensions, extending radially from said axis, comprising the steps of:
    inserting said finger into a vagina of a patient so that said projection reaches into and onto an indocervix and cervix;
    rotating said finger a half turn in a circular motion about an axis of said projections to remove a sample from said patient; and
    withdrawing said finger from said patient.

* * * * *